(12) United States Patent
Yorozu et al.

(10) Patent No.: US 12,137,962 B2
(45) Date of Patent: *Nov. 12, 2024

(54) SURGICAL ELECTRODE HAVING SURFACE TREATMENT COATING

(71) Applicant: Nihon Parkerizing Co., Ltd., Tokyo (JP)

(72) Inventors: Takayuki Yorozu, Tokyo (JP); Junichi Uchida, Tokyo (JP); Ryoko Katsuraya, Tokyo (JP); Motoki Komaike, Tokyo (JP)

(73) Assignee: Nihon Parkerizing Co., Ltd., Tokyo (JP)

( * ) Notice: Subject to any disclaimer, the term of this patent is extended or adjusted under 35 U.S.C. 154(b) by 728 days.

This patent is subject to a terminal disclaimer.

(21) Appl. No.: 17/265,050

(22) PCT Filed: Aug. 5, 2019

(86) PCT No.: PCT/JP2019/030640
§ 371 (c)(1),
(2) Date: Feb. 1, 2021

(87) PCT Pub. No.: WO2020/027341
PCT Pub. Date: Feb. 6, 2020

(65) Prior Publication Data
US 2021/0307809 A1 Oct. 7, 2021

(30) Foreign Application Priority Data
Aug. 3, 2018 (JP) .................................. 2018-147135

(51) Int. Cl.
*A61B 18/12* (2006.01)
*A61B 18/14* (2006.01)
(Continued)

(52) U.S. Cl.
CPC ................ *A61B 18/14* (2013.01); *C09D 7/20* (2018.01); *C09D 7/61* (2018.01); *C09D 7/63* (2018.01);
(Continued)

(58) Field of Classification Search
CPC . A61B 18/14; A61B 18/1402; A61B 18/1482; C23C 28/00; C09D 179/02;
(Continued)

(56) References Cited

U.S. PATENT DOCUMENTS 4,347,346 A * 8/1982 Eckberg ................. D21H 19/32
428/447
4,785,807 A 11/1988 Blanch
(Continued)

FOREIGN PATENT DOCUMENTS

CN 1279984 C 10/2006
CN 102090923 A 6/2011
(Continued)

OTHER PUBLICATIONS

Search Report in International Application No. PCT/JP2019/030640 dated Aug. 27, 2019, 2 pages.
(Continued)

*Primary Examiner* — Daniel W Fowler
(74) *Attorney, Agent, or Firm* — MARSHALL, GERSTEIN & BORUN LLP

(57) ABSTRACT

Provided is a surgical electrode in which an end portion capable of emitting a high frequency has a surface treatment film that includes a first coating and a second film in the order mentioned. The first coating is formed by contacting a surface treatment agent (X) with or over the entirety or a part of the surface of the end portion at least, which surface treatment agent (X) contains at least an amino group-containing compound, and the second film is formed by
(Continued)

contacting a surface treatment agent (Y) with a part or the entirety of the surface of the first coating, which surface treatment agent (Y) contains: a silicone resin (A); a compound (B) containing a metal element selected from titanium, platinum, rhodium and palladium; and an aromatic hydrocarbon-based solvent (C), and satisfies: (I) the content of the silicone resin is in a range of 90% by mass to 99.9% by mass with respect to a total solid mass of the silicone resin and the compound; and (II) a ratio ($B_M/A_M$) of a mass ($B_M$) of the compound to a mass ($A_M$) of the silicone resin is in a range of 0.001 to 0.111.

3 Claims, 14 Drawing Sheets

(51) Int. Cl.
    *C09D 7/20*      (2018.01)
    *C09D 7/61*      (2018.01)
    *C09D 7/63*      (2018.01)
    *C09D 179/00*    (2006.01)
    *C09D 179/02*    (2006.01)
    *C09D 183/06*    (2006.01)
    *C23C 28/00*     (2006.01)
    *A61B 18/00*     (2006.01)

(52) U.S. Cl.
    CPC ......... *C09D 179/02* (2013.01); *C09D 183/06* (2013.01); *C23C 28/00* (2013.01); *A61B 2018/00136* (2013.01); *A61B 2018/00148* (2013.01); *A61B 2018/1407* (2013.01); *A61B 2018/1412* (2013.01); *A61B 2018/1417* (2013.01); *A61B 2018/1422* (2013.01); *A61B 2018/1425* (2013.01)

(58) Field of Classification Search
    CPC ...... C09D 183/04; C09D 183/06; C09D 7/20; C09D 7/61; C09D 7/63
    See application file for complete search history.

(56) References Cited

U.S. PATENT DOCUMENTS

| | | | |
|---|---|---|---|
| 6,063,083 A * | 5/2000 | Duong-Van | A61B 18/1402 607/101 |
| 6,070,444 A | 6/2000 | Lontine et al. | |
| 9,434,857 B2 * | 9/2016 | Ou | B01J 31/2282 |
| 2005/0245924 A1 * | 11/2005 | Swoyer | A61B 18/14 606/41 |
| 2010/0278771 A1 | 11/2010 | Lobe et al. | |
| 2012/0114957 A1 | 5/2012 | Fujibayashi et al. | |
| 2013/0340992 A1 | 12/2013 | Akinaga et al. | |
| 2014/0145230 A1 * | 5/2014 | Matsuda | C09D 183/14 428/447 |
| 2014/0336642 A1 | 11/2014 | Nesbitt | |
| 2016/0368246 A1 * | 12/2016 | Yamaguchi | B32B 17/1055 |
| 2017/0210899 A1 * | 7/2017 | Yoshikawa | C09K 3/10 |
| 2017/0290623 A1 | 10/2017 | Miki et al. | |
| 2018/0353658 A1 | 12/2018 | Murano et al. | |

FOREIGN PATENT DOCUMENTS

| | | |
|---|---|---|
| CN | 102378827 A | 3/2012 |
| CN | 103443223 A | 12/2013 |
| CN | 206852656 U | 1/2018 |
| EP | 3696297 A1 | 8/2020 |
| JP | 2000-333968 A | 12/2000 |
| JP | 2010-207930 A | 9/2010 |
| JP | 2010-227462 A | 10/2010 |
| JP | 2017-148479 A | 8/2017 |
| WO | WO-03/068289 A1 | 8/2003 |
| WO | WO-2016/051918 A1 | 4/2016 |

OTHER PUBLICATIONS

Extended European Search Report in EP Application No. 19844985.2 dated Apr. 8, 2022, 8 pages.
Office Action in IN Application No. 202117004321 dated Apr. 15, 2021, 5 pages.
Office Action and Search Report in CN Application No. 201980050171.6 dated Feb. 1, 2024, 8 pages.

* cited by examiner

SURGICAL ELECTRODE HAVING SURFACE TREATMENT COATING

TECHNICAL FIELD

The present invention relates to a surgical electrode having a surface treatment film, which can be preferably used in an electrosurgical instrument that is used for surgery of a living tissue as a medical device.

BACKGROUND ART

In surgical procedures, an electrosurgical instrument (so-called electric cautery) which can perform hemostasis (coagulation) and incision by discharging a high-frequency electric current generated by its main body from a surgical electrode to a living tissue is indispensable. The use of an electric cautery is known to have a problem of causing an "eschar" in which carbides of a living tissue and the like adhere to the tip of the electric cautery and, with regard to this problem, there has been proposed a method of mass-producing plural electrodes that can each be connected to an appropriate electrical power source for surgical procedure, which method is characterized by including the steps of: preparing an electroconductive stock material that has a shape and dimensions for forming plural electrode blanks; coating at least a part of the stock material with a non-stick layer; and forming plural coated electrode blanks (see Patent Document 1).

RELATED ART DOCUMENT

Patent Document

[Patent Document 1] Japanese Unexamined Patent Application Publication No. 2000-333968

SUMMARY OF THE INVENTION

Problems to be Solved by the Invention

However, the technology disclosed in Patent Document 1 was found to have a problem that the coated non-stick layer is damaged by Joule heat and discharge voltage associated with a high-frequency electric current released from the tip of an electric cautery, and the non-stick layer is consequently peeled off or eliminated.

The present invention solves this problem, and an object of the present invention is to provide a surgical electrode of an electrosurgical instrument used for surgery of a living tissue, the surgical electrode having a film to which carbides of the living tissue and the like are unlikely to adhere and which has excellent adhesion with the surgical electrode.

Means for Solving the Problems

The present inventors intensively studied to solve the above-described problem and consequently discovered that a film to which carbides of a living tissue and the like are unlikely to adhere and which has excellent adhesion with a surgical electrode can be provided by incorporating a base coating, which is formed from a surface treatment agent containing at least an amino group-containing compound, between a silicone resin-based film and the surgical electrode, thereby completing the present invention.

That is, the present invention can encompass the followings.

<1> A surgical electrode of an electrosurgical instrument used for surgery of a living tissue,
wherein
the surgical electrode includes an end portion capable of emitting a high frequency,
the end portion has a surface treatment film which includes a first coating and a second film in the order mentioned,
the first coating is formed by contacting a surface treatment agent (X) with or over the entirety or a part of the surface of the end portion at least, which surface treatment agent (X) contains at least an amino group-containing compound, and
the second film is formed by contacting a surface treatment agent (Y) with the entirety or a part of the surface of the first coating, which surface treatment agent (Y) contains: a silicone resin (A); a compound (B) containing a metal element selected from titanium, platinum, rhodium and palladium; and an aromatic hydrocarbon-based solvent (C), and satisfies:
(I) the content of the silicone resin (A) is in a range of 90% by mass to 99.9% by mass with respect to a total solid mass of the silicone resin (A) and the compound (B); and
(II) a ratio ($B_M/A_M$) of a mass ($B_M$) of the compound (B) to a mass ($A_M$) of the silicone resin (A) is in a range of 0.001 to 0.111.
<2> The surgical electrode according to <1>, wherein the surface treatment agent (Y) further contains a vinyl group-containing silane coupling agent and/or an epoxy group-containing silane coupling agent, and a ratio ($D_M/A_M$) of a total mass ($D_M$) of the vinyl group-containing silane coupling agent and the epoxy group-containing silane coupling agent to the mass ($A_M$) is in a range of 0.005 to 0.251.

Effects of the Invention

According to the present invention, a surgical electrode of an electrosurgical instrument used for surgery of a living tissue, the surgical electrode having a film to which carbides of the living tissue and the like are unlikely to adhere and which has excellent adhesion with the surgical electrode, can be provided.

BRIEF DESCRIPTION OF THE DRAWINGS

FIG. 5A illustrates a wire L-shaped hook type.

FIG. 5B illustrates a straight spatula type.

FIG. 5C illustrates a wire J-shaped hook type.

FIG. 5D illustrates a syringe type.

MODE FOR CARRYING OUT THE INVENTION

The surgical electrode having a surface treatment film according to one embodiment of the present invention includes: a surgical electrode of an electrosurgical instrument used for surgery of a living tissue; and a surface treatment film which includes a first coating and a second film in this order on or over the surface of the surgical electrode. The surgical electrode may, but not required to, further include a passivation film and/or an oxide film of a metal contained in the surgical electrode between the surgical electrode and the first coating.

<Surgical Electrode>

Figure 1:
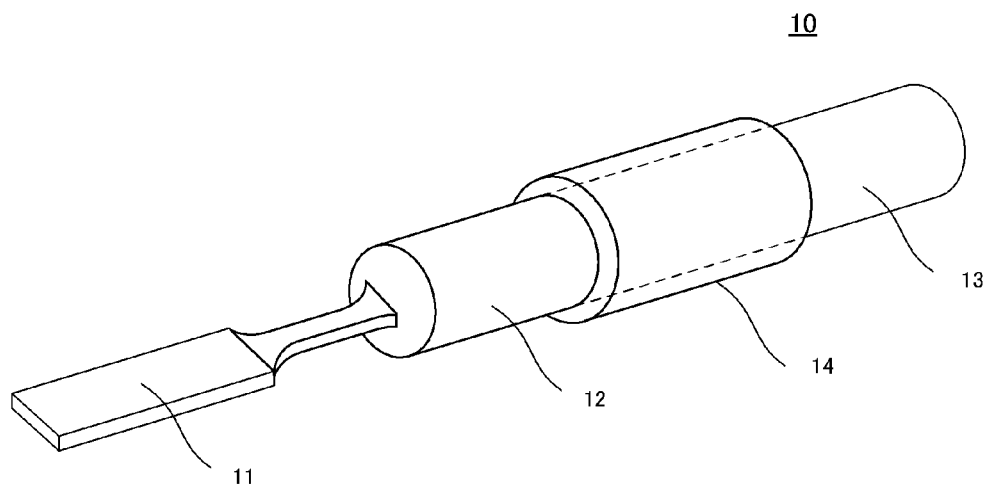
FIG. 1 is a schematic drawing that illustrates one example (blade electrode) of a surgical electrode (electric cautery).

The surgical electrode is an electrode to be fitted onto a tip of an electrosurgical instrument such as a so-called electric cautery in a detachable manner, and is capable of performing hemostasis (coagulation) and incision of a living tissue by emitting a high frequency to the living tissue from an end portion of the electrode. The surgical electrode is composed of an electroconductive material. More specifically, examples of the electroconductive material include iron-based metal materials, zinc-plated metal materials, aluminum-based metal materials, magnesium-based metal materials, nickel-based metal materials, titanium-based metal materials, zirconium-based metal materials, copper-based metal materials, tin-based metal materials, tungsten-based metal materials, chromium-based metal materials, manganese-based metal materials, molybdenum-based metal materials and cobalt-based metal materials, and the electroconductive material is more preferably a stainless steel. Typical examples of an electrosurgical instrument to which the surgical electrode is fitted include electric cauteries such as monopolar cauteries and bipolar cauteries, and laparoscopes. FIG. 1 is a schematic drawing that illustrates one example of the surgical electrode.

FIG. 1 illustrates one example of a blade-type surgical electrode whose end portion is in a plate form.

A surgical electrode 10 is a member which can be attached to and detached from an electrosurgical instrument main body (not illustrated). The surgical electrode 10 is constituted by: an electrical connection portion 13, which is electrically connected to the electrosurgical instrument main body; an end portion 11, which is brought into close contact with a living tissue and from which a high frequency is emitted; and an intermediate portion 12, which connects the electrical connection portion 13 and the end portion 11.

<End Portion>

Figure 2:
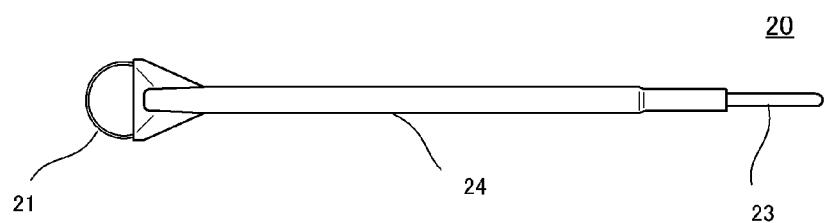
FIG. 2 is a schematic drawing that illustrates another example (loop-type electrode) of a surgical electrode (electric cautery).
Figure 3:
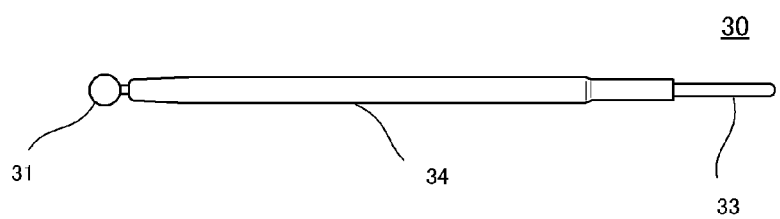
FIG. 3 is a schematic drawing that illustrates yet another example (ball-type electrode) of a surgical electrode (electric cautery).
Figure 4:
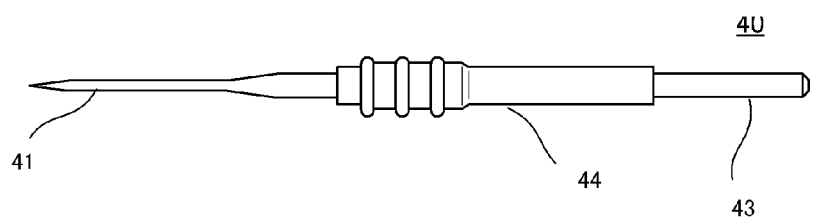
FIG. 4 is a schematic drawing that illustrates yet another example (needle-type electrode) of a surgical electrode (electric cautery).
Figure 5A:
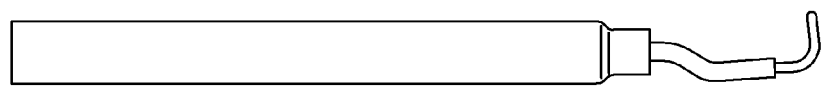
FIG. 5A provides a schematic drawing that illustrates an example of a surgical electrode (laparoscope).
Figure 5B:
FIG. 5B provides a schematic drawing that illustrates an example of a surgical electrode (laparoscope).
Figure 5C:
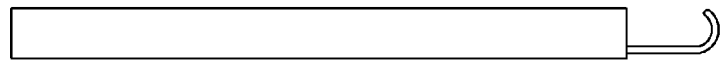
FIG. 5C provides a schematic drawing that illustrates an example of a surgical electrode (laparoscope).
Figure 5D:
FIG. 5D provides a schematic drawing that illustrates an example of a surgical electrode (laparoscope).
Figure 6:
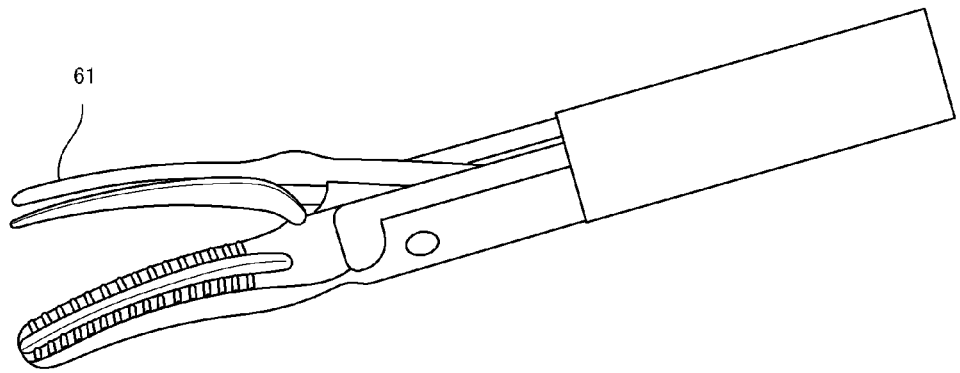
FIG. 6 is a schematic drawing that illustrates yet another example (bipolar-type) of a surgical electrode (electric cautery).

The end portion 11 is a part which is brought into close contact with a living tissue and from which a high frequency is emitted. The shape of the end portion is not particularly restricted, and examples of the end portion include: the end portion 11 of the blade-type surgical electrode 10 illustrated in FIG. 1; an end portion 21 of a loop-type surgical electrode 20 illustrated in FIG. 2; an end portion 31 of a ball-type surgical electrode 30 illustrated in FIG. 3; and an end portion 41 of a needle-type surgical electrode 40 illustrated in FIG. 4, and these surgical electrodes are used as tip electrodes of electric cauteries. In addition, there are surgical electrodes fitted to a laparoscope, such as a wire L-shaped hook-type electrode illustrated in FIG. 5A, a straight spatula-type electrode illustrated in FIG. 5B, a wire J-shaped hook-type electrode illustrated in FIG. 5C, and a syringe-type electrode illustrated in FIG. 5D. The above-described end portions are each an end portion of a monopolar-type surgical electrode; however, they may each be an end portion of a bipolar-type surgical electrode. FIG. 6 illustrates one example of an end portion 61 of a bipolar-type surgical electrode 60.

In the end portion 11, a roughening treatment may or may not be performed on at least a part (e.g., a part where the below-described first coating is formed, or a part where the below-described second film is formed) of the surface of the electroconductive material. Examples of a method for performing the roughening treatment include, but not limited to: a shot blasting method, an etching method using a solution (e.g., an acidic solution or an alkaline solution), a grinding method, a plasma treatment method, and a corona discharge treatment method. These treatments may be performed singly, or two or more thereof may be performed in combination. The surface roughness of the end portion 11 is preferably in a range of 0.05 μm to 0.39 μm, more preferably in a range of 0.08 μm to 0.25 μm, particularly preferably in a range of 0.10 μm to 0.18 μm, in terms of arithmetic average roughness Ra. The term "surface roughness" used herein means line roughness, and the above-described Ra is a value measured by a contact-type surface roughness meter.

<Electrical Connection Portion>

The electrical connection portion 13 of the surgical electrode 10 is a part which is electrically connected to a main body of an electrosurgical instrument. The electrical connection portion 13 can be attached to or detached from the main body of the electrosurgical instrument, and is usually configured such that it can be fitted with the main body of the electrosurgical instrument by a mating structure or the like. The electrical connection portion is also composed of an electroconductive material, which may be the same as or different from that of the end portion 11.

<Intermediate Portion>

The intermediate portion 12 is a member which connects the end portion 11 to the electrical connection portion 13. The intermediate portion 12 is required to be composed of an electroconductive material for electrical conduction to the end portion 11; however, the shape, the length and the like of the intermediate portion 12 are not particularly restricted.

The intermediate portion 12 may have a cover 14. The cover 14 is a cured product of a composition containing an insulating resin. Further, the size, the thickness, the shape and the like of the cover 14 are not particularly restricted as long as the intermediate portion 12 and the cover 14 are in contact with each other.

<Surface Treatment Film>

The surface treatment film according to the present embodiment includes a first coating and a second film. The first coating is formed by contacting a surface treatment agent (X) with or over the surface of the surgical electrode (a part or the entirety of the end portion at least), and the second film is formed by contacting a surface treatment agent (Y) with a part or the entirety of the surface of the first coating.

The surface treatment film may be formed at least on the entire surface of the end portion, or on a part of the end portion. In the case of a blade-type surgical electrode, examples of the "part" include the blade part of the end portion, and the flat part of the end portion. The term "flat part" used herein refers to a part having the largest area in the blade part of the end portion 11 illustrated in FIGS. 7A-C.

In those parts where the surface treatment film is not formed, only the first coating may be formed. For example, in the case of a blade-type surgical electrode, the first coating may be formed on the entire surface of the blade part, and the second film may be formed partially on the first coating. Further, in the end portion 11, only the first coating or both the first coating and the second film may be formed on a part or the entirety of the surface of the end part (hereinafter, referred to as "intermediate connecting part") on the side of the intermediate portion 12.

<Surface Treatment Agent (X)>

The surface treatment agent (X) according to the present embodiment contains at least an amino group-containing compound. The amino group-containing compound is not particularly restricted. The amino group may be any of a primary amino group, a secondary amino group and a tertiary amino group, and the amino group-containing compound may be one which has two or more of these amino groups. Specifically, the amino group-containing compound may be, for example, an amine-based curing agent; a homopolymer of a glycidylamine-type epoxy resin, a homopolymer of a polyethyleneimine resin, a homopolymer of a melamine resin, a homopolymer of an aromatic amine resin or the like, or a copolymer containing these polymers; or an amino group-containing silane coupling agent. Examples of the amine-based curing agent include, but not limited to: dicyandiamide, diethylenetriamine, N-aminoethylpiperazine, m-phenylenediamine, 2-methylimidazole, and 2-ethyl-4-methylimidazole. In the case of using an amine-based curing agent, it is preferred to use it in combination with an epoxy resin.

The amino group-containing silane coupling agent is not particularly restricted as long as it has one amino group, and examples thereof include N-2-(aminoethyl)-3-aminopropyldimethylmethoxysilane, N-2-(aminoethyl)-3-aminopropylmethyldimethoxysilane, N-2-(aminoethyl)-3-aminopropyltrimethoxysilane, N-2-(aminoethyl)-3-aminopropyldiethylethoxysilane, N-2-(aminoethyl)-3-aminopropylethyldiethoxysilane, N-2-(aminoethyl)-3-aminopropyltriethoxysilane, 3-aminopropyldimethylmethoxysilane, 3-aminopropylmethyldimethoxysilane, 3-aminopropyltrimethoxysilane, 3-aminopropyldiethylethoxysilane, 3-aminopropylethyldiethoxysilane, 3-aminopropyltriethoxysilane, N-phenyl-3-aminopropyltrimethoxysilane, and 3-triethoxysilyl-N-(1,3-dimethyl-butylidene) propylamine.

A solvent contained in the surface treatment agent (X) is not particularly restricted, and examples thereof include organic solvents, such as alcohols, acetone, acetonitrile, benzene, cyclohexane, methyl acetate, ethyl acetate, and methyl ethyl ketone; and mixtures of these organic solvents and water. As an organic solvent, an alcohol having not more than 5 carbon atoms is preferred. When the solvent is a mixture of an organic solvent and water, the mass ratio of water contained in the mixture is preferably less than 5% by mass; however, it is more preferred that the solvent contains substantially no water.

Further, the surface treatment agent (X) may also contain additives, such as a leveling agent used for improving the wettability, a film-forming aid used for improving the film-forming properties, an organic or inorganic crosslinking agent used for obtaining a more rigid film, an antifoaming agent used for inhibiting foam formation, a thickening agent used for controlling the viscosity, and a rust inhibitor. These additives may be incorporated within a range that does not impair the effects of the present invention.

In the surface treatment agent (X), the total content of the amino group-containing compound is not particularly restricted; however, it is preferably in a range of 0.1% by mass to 10% by mass, more preferably in a range of 0.5% by mass to 5% by mass, with respect to a total amount of the surface treatment agent (X).

<Surface Treatment Agent (Y)>

The surface treatment agent (Y) according to the present embodiment contains: a silicone resin (A); a compound (B) containing a metal element selected from titanium, platinum, rhodium and palladium; and an aromatic hydrocarbon-based solvent (C). By using this surface treatment agent (Y), a surface treatment film to which a carbide of a living tissue is unlikely to adhere can be formed.

<Silicone Resin (A)>

The silicone resin (A) is not particularly restricted as long as it has an organopolysiloxane structure which contains plural siloxane bonds and in which an organic group is bound to silicon (Si); however, the silicone resin (A) preferably has an organopolysiloxane structure which contains at least two or more organic groups bound to Si in one molecule. The position at which each organic group is bound is not particularly restricted, and each organic group may be bound to a main chain, a side chain, or a terminal. The silicone resin (A) may be a homopolymer having the above-described organopolysiloxane structure, a mixture of a homopolymer having the above-described organopolysiloxane structure and a homopolymer having a polysiloxane structure, or a copolymer (a block copolymer or a graft polymer) that has the above-described organopolysiloxane structure and a polysiloxane structure. Further, the silicone resin (A) may be of an addition type or a condensation type. Moreover, the silicone resin (A) may be any of a thermosetting type, a room temperature-curable type (RTV), and a UV-curable type.

Examples of the organic group bound to Si in the organopolysiloxane structure include, but not limited to: saturated hydrocarbon groups, unsaturated hydrocarbon groups, halogenated alkyl groups, and an epoxycyclohexyl group. Examples of the saturated hydrocarbon groups include, but not limited to: linear or branched alkyl groups and cycloalkyl groups. Examples of the unsaturated hydrocarbon groups include, but not limited to: linear or branched alkenyl groups, cycloalkenyl groups, cycloalkenylalkyl groups, and aryl groups. The organic group bound to Si is preferably an unsaturated hydrocarbon group, more preferably an alkenyl group, particularly preferably a vinyl group or a hexenyl group.

Examples of the halogenated alkyl groups include a chloromethyl group, a 3-chloropropyl group, a 1-chloro-2-methylpropyl group, and a 3,3,3-trifluoropropyl group. Examples of the alkyl groups include a methyl group, an ethyl group, a propyl group, a butyl group, a pentyl group, a hexyl group, a heptyl group, an octyl group, a nonyl group, and a decyl group. Examples of the cycloalkyl groups include a cyclopentyl group and a cyclohexyl group. Examples of the linear or branched alkenyl groups include a vinyl group, a 1-propenyl group, an allyl group, an isopropenyl group, a 1-butenyl group, a 2-butenyl group, a pentenyl group, and a hexenyl group. Examples of the cycloalkenyl groups include a cyclopentenyl group and a cyclohexenyl group. Examples of the cycloalkenylalkyl groups include a cyclopentenylethyl group, a cyclohexenylethyl group, and cyclohexenylpropyl group. Examples of the aryl groups include a phenyl group.

The polysiloxane structure is not particularly restricted as long as it is different from the above-described organopolysiloxane structure, and examples thereof include a polysiloxane structure that contains at least two or more hydrogen atoms bound to Si in one molecule, and a polysiloxane structure that contains at least two or more alkoxy groups bound to Si in one molecule. Examples of the alkoxy groups include a methoxy group, an ethoxy group, a propoxy group, and a butoxy group. The alkoxy groups may each be linear or branched.

In the preparation of the surface treatment agent (Y), the above-described various silicone resins may be used singly, or in combination of two or more thereof. One example of a preferred embodiment of the silicone resin (A) is a mixture of a polymer having an organopolysiloxane structure that contains at least two or more unsaturated hydrocarbon groups bound to Si in one molecule and a polymer having a polysiloxane structure that contains at least two or more hydrogen atoms bound to Si in one molecule.

Examples of the polymer having an organopolysiloxane structure that contains at least two or more unsaturated hydrocarbon groups bound to Si in one molecule include a dimethyl polysiloxane having dimethylvinyl siloxy groups at both terminals of its molecular chain, a dimethyl siloxane-methylphenyl siloxane copolymer having dimethylvinylsiloxy groups at both terminals of its molecular chain, a dimethyl siloxane-methylvinyl siloxane copolymer having dimethylvinylsiloxy groups at both terminals of its molecular chain, a dimethyl siloxane-methylvinyl siloxane copolymer having trimethylsiloxy groups at both terminals of its molecular chain, a dimethyl siloxane-methylvinyl siloxane-methylphenyl siloxane ternary copolymer having trimethylsiloxy groups at both terminals of its molecular chain, a dimethyl siloxane-methylvinyl siloxane copolymer having silanol groups at both terminals of its molecular chain, and a methylvinyl polysiloxane having silanol groups at both terminals of its molecular chain, as well as polymers in which some of the methyl groups of various homopolymers, copolymers and ternary copolymers are substituted with: alkyl groups other than a methyl group, such as an ethyl group and a propyl group; or halogenated alkyl groups, such as a 3,3,3-trifluoropropyl group and a 3,3,3-trichloropropyl group. A mixture of two or more selected from the above-described homopolymers, copolymers and ternary copolymers may be used for the preparation of the surface treatment agent (Y).

The polymer having a polysiloxane structure that contains at least two or more hydrogen atoms bound to Si in one molecule is not particularly restricted, and examples thereof include organohydrogen polysiloxanes having a linear, cyclic, branched or three-dimensional network structure which contains at least two or more SiH groups, in each of which a hydrogen atom is bound to Si, in one molecule and has repeating diorganosiloxane units as a main chain and whose molecular chains are capped with triorganosiloxy groups at both terminals. More specific examples include a methyl hydrogen polysiloxane having trimethylsiloxy groups at both terminals of its molecular chain, a dimethyl siloxane-methyl hydrogen siloxane copolymer having trimethylsiloxy groups at both terminals of its molecular chain, a methyl hydrogen polysiloxane having silanol groups at both terminals of its molecular chain, a dimethyl siloxane-methyl hydrogen siloxane copolymer having silanol groups at both terminals of its molecular chain, a dimethyl polysiloxane having dimethyl hydrogen siloxy groups at both terminals of its molecular chain, a methyl hydrogen polysiloxane having dimethyl hydrogen siloxy groups at both terminals of its molecular chain, and a dimethyl siloxane-methyl hydrogen siloxane copolymer having dimethyl hydrogen siloxy groups at both terminals of its molecular chain. A mixture of two or more selected from the above-described homopolymers and copolymers may be used for the preparation of the surface treatment agent (Y).

The weight-average molecular weight of the silicone resin (A) is not particularly restricted; however, it is usually in a range of 6,000 to 45,000, preferably in a range of 6,500 to 40,000. The weight-average molecular weight is a value measured by GPC (gel permeation chromatography) in terms of polystyrene.

<Compound (B)>

The compound (B) is not particularly restricted as long as it is a compound that contains a metal element selected from titanium, platinum, rhodium, and palladium. Examples of a compound containing titanium include titanyl sulfate, titanyl nitrate, titanium nitrate, titanyl chloride, titanium chloride, titania sol, titanium oxide, titanium potassium oxalate, titanium lactate, titanium tetraisopropoxide, titanium acetylacetonate, diisopropyl titanium bis-acetylacetone, and titanium diisopropoxy-bis (acetylacetonate).

Examples of a compound containing platinum, rhodium, or palladium include simple metals of platinum group, such as platinum (including platinum black), rhodium, and palladium; platinum chloride, chloroplatinic acid and chloroplatinates, such as $H_2PtCl_4 \cdot nH_2O$, $H_2PtCl_6 \cdot nH_2O$, $NaHPtCl_6 \cdot nH_2O$, $KHPtCl_6 \cdot nH_2O$, $Na_2PtCl_6 \cdot nH_2O$, $K_2PtCl_4 \cdot nH_2O$, $PtCl_4 \cdot nH_2O$, $PtCl_2$, and $Na_2HPtCl_4 \cdot nH_2O$ (wherein, n is an integer of 0 to 6, preferably 0 or 6); alcohol-modified chloroplatinic acid (reaction product of an alcohol and chloroplatinic acid); complexes of chloroplatinic acid with olefins; compounds in which a platinum-group metal, such as platinum black or palladium, is supported on a carrier such as alumina, silica, or carbon; rhodium-olefin complexes; chlorotris (triphenyl phosphine) rhodium (Wilkinson's catalyst); complexes of platinum chloride, chloroplatinic acid or a chloroplatinate with vinyl-containing siloxane; and compounds in which platinum chloride is supported on a polystyrene-polyethylene glycol.

In the preparation of the surface treatment agent (Y), these compounds may be used singly, or in combination of two or more thereof.

The content of the silicone resin (A) (which means a total content when plural silicone resins are used) is in a range of 90% by mass to 99.9% by mass, preferably in a range of 95% by mass to 99.8% by mass, more preferably in a range of 98% by mass to 99.7% by mass, with respect to a total solid mass of the silicone resin (A) and the compound (B).

In the surface treatment agent (Y), a ratio ($B_M/A_M$) of the mass ($B_M$) of the compound (B) [which means a total mass when plural compounds are used] to the mass ($A_M$) of the silicone resin (A) [which means a total mass when plural silicone resins are used] is preferably in a range of 0.001 to 0.111, more preferably in a range of 0.002 to 0.053, particularly preferably in a range of 0.003 to 0.02.

<Aromatic Hydrocarbon-Based Solvent (C)>

The aromatic hydrocarbon-based solvent (C) is a hydrocarbon constituted by, as a unit, a single ring or plural planar rings that is/are composed of six carbon atoms with alternating single and double bonds and delocalized electrons, and the type of the hydrocarbon is not particularly restricted.

The aromatic hydrocarbon-based solvent (C) is not particularly restricted as long as it contains the above-described unit; however, the aromatic hydrocarbon-based solvent (C) has a solubility parameter (SP) value in a range of preferably 8.5 to 9.5, more preferably 8.8 to 9.3. More specific examples of the aromatic hydrocarbon-based solvent (C) include benzene, toluene, o-xylene, p-xylene, m-xylene, para-xylene, and ortho-xylene. In the preparation of the surface treatment agent (Y), these aromatic hydrocarbon-based solvents (C) may be used singly, or in combination of two or more thereof.

In the surface treatment agent (Y), the content of the aromatic hydrocarbon-based solvent (C) is not particularly restricted; however, it is preferably in a range of 40% by mass to 99% by mass, more preferably in a range of 45% by mass to 95% by mass, particularly preferably in a range of 50% by mass to 80% by mass, most preferably in a range of 60% by mass to 75% by mass, in terms of mass ratio.

<Other Additives>

The surface treatment agent (Y) according to the present embodiment may also contain various additives as required. Examples of the additives include, but not limited to: a surfactant, an antifoaming agent, a leveling agent, a thickening agent, an antibacterial and antifungal agent, a colorant, and a fluorine resin. These additives may be added within a range that does not impair the effects of the present invention, and the content of the additives is at most several % by mass with respect to the mass of the surface treatment agent (Y).

In the surface treatment agent (Y), a silane coupling agent (D), such as a vinyl group-containing silane coupling agent and/or an epoxy group-containing silane coupling agent, may be incorporated as well. The vinyl group-containing silane coupling agent is not particularly restricted as long as it is a silane coupling agent that contains a vinyl group, and examples thereof include vinyl group-containing silane coupling agents, such as vinyltrimethoxysilane, vinyltriethoxysilane, and p-styryltrimethoxysilane. The epoxy group-containing silane coupling agent is also not particularly restricted as long as it is a silane coupling agent that contains an epoxy group, and examples thereof include epoxy group-containing silane coupling agents, such as 3-glycidoxypropyltrimethoxysilane, 3-glycidoxypropylmethyldimethoxysilane, and 2-(3,4-epoxycyclohexyl) ethyltrimethoxysilane. When an epoxy group-containing silane coupling agent is used by itself or in combination with a vinyl group-containing silane coupling agent, it is preferred to use a silane coupling agent having a single epoxy group as the epoxy group-containing silane coupling agent.

When a silane coupling agent is used in the preparation of the surface treatment agent (Y), a ratio ($D_M/A_M$) of the mass ($D_M$) of the silane coupling agent (D) [which means a total mass when plural silane coupling agents are used] to the mass ($A_M$) of the silicone resin (A) [which means a total mass when plural silicone resins are used] is preferably in a range of 0.005 to 0.251, more preferably in a range of 0.01 to 0.11; however, the ratio ($D_M/A_M$) is not restricted to be in this range.

The surface treatment agent (Y) according to the present embodiment can be produced by mixing the silicone resin (A), the compound (B) containing a metal element selected from titanium, platinum, rhodium and palladium, and the aromatic hydrocarbon-based solvent (C) along with, as required, additives such as the silane coupling agent (D). In the case of using the surface treatment agent (Y) according to the present embodiment for the below-described surface treatment, the viscosity of the surface treatment agent (Y) at 25° C. is preferably in a range of 1 Pa·s to 30 Pa·s, more preferably in a range of 3 Pa·s to 20 Pa·s, particularly preferably in a range of 5 Pa·s to 15 Pa·s. The viscosity of the surface treatment agent (Y) can be measured using a vibration-type viscometer (VM Series, manufactured by Sekonic Corporation).

<Surgical Electrode Having Surface Treatment Film and Production Method Thereof>

The surgical electrode having a surface treatment film according to the present embodiment can be produced by, for example, the following method. The method includes: the first step of contacting the surface treatment agent (X) with or over a surface (a part or the entirety of an end portion at least) of a molded surgical electrode; and the second step of forming a first coating by drying the surface treatment agent (X) brought into contact with the surface of the surgical electrode. By performing these steps, a surgical electrode having the first coating can be produced.

Prior to the first step, for the purposes of forming irregularities on the surface of the surgical electrode and removing oil, dirt and oxide films adhering to the surface of the metal material, a pretreatment may be performed on the metal material. A method for this pretreatment is not particularly restricted, and examples thereof include: a roughening treatment, such as a shot blasting treatment, an etching treatment using a solution (e.g., an acidic solution or an alkaline solution), a grinding treatment, a plasma treatment, or a corona discharge treatment; a washing treatment, such as hot-water washing, solvent washing, alkali degreasing, or acid pickling; an oxide film removing treatment, and a water-washing treatment. These treatments may be performed singly, or two or more thereof may be performed in combination.

As a contact method in the first step, a variety of contact methods can be employed, and an optimum method can be selected as appropriate in accordance with, for example, the shape of the surgical electrode. Specific examples of the contact method include, but not limited to: a coating method using a coating apparatus, an immersion treatment method, a spray treatment method, a pouring method, a roll coating method, and a bar coating method.

Further, examples of a drying method employed in the second step include, but not limited to: a method of drying the surface treatment agent (X) using a hot-air or induction heater, or with infrared ray, near-infrared ray or the like; and a method of drying the surface treatment agent (X) by vacuum distillation. The drying temperature is not particularly restricted; however, it is preferably in a range of 40 to 250° C., more preferably in a range of 60 to 180° C. The drying time is also not particularly restricted, and may be changed as appropriate in accordance with, for example, the types of the materials to be used, and the amount of the surface treatment agent (X) adhering on or over the surface of the surgical electrode.

The method of producing the surgical electrode having a surface treatment film according to the present embodiment further includes: the third step of contacting the surface treatment agent (Y) with a part or the entirety of the surface of the first coating formed on the surgical electrode; and the fourth step of forming a second film by drying the surface treatment agent (Y) brought into contact with the first coating. By performing these steps, a surface treatment film that includes the first coating and the second film in this order can be formed on the surgical electrode.

As a contact method in the third step, a variety of contact methods can be employed, and an optimum method can be selected as appropriate in accordance with, for example, the shape of the surgical electrode to be treated. Specific examples of the contact method include coating methods, such as an immersion treatment method, a spray treatment method, a pouring method, a roll coating method, and a bar coating method; and coating methods using one or more coating apparatuses, such as a spin coater, a slit coater, a die coater, a blade coater, and a dispenser.

The drying temperature in the fourth step is not particularly restricted; however, it is preferably in a range of 40 to 250° C., more preferably in a range of 60 to 180° C. A drying method is not particularly restricted, and examples thereof include a method of drying the surface treatment agent (Y) using a hot-air or induction heater, or with infrared ray, near-infrared ray or the like; and a method of drying the surface treatment agent (Y) by vacuum distillation. The drying time is also not particularly restricted, and can be set as appropriate in accordance with, for example, the types of the materials to be used, and the amount of the surface treatment agent (Y) adhering on or over the surface of the surgical electrode. The drying time may be, for example, 10 minutes or longer, or 15 minutes or longer, but 60 minutes or shorter, or 30 minutes or shorter.

By performing the above-described first to fourth steps, a surface treatment film that includes the first coating and the second film in this order can be formed on the surgical electrode. The part where the first coating is formed and the part where the second film is formed may be in the same region or different regions. It is noted here that the first coating exists as an underlayer in the part where the second film is formed.

Figure 7A:
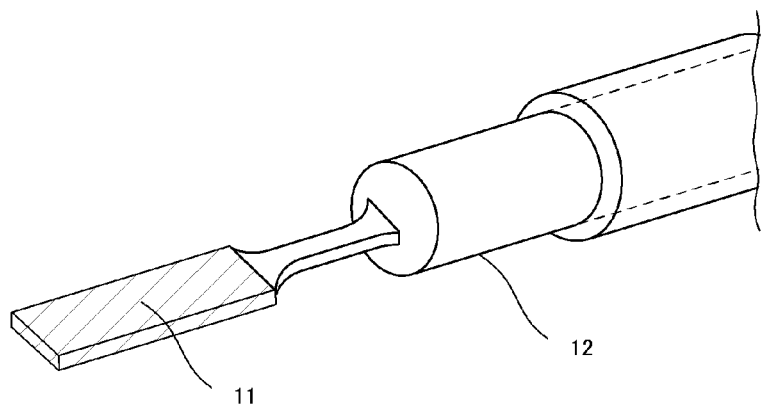
FIG. 7A provides a schematic drawing that illustrates a formation example of a first coating on a surgical electrode.
Figure 7B:
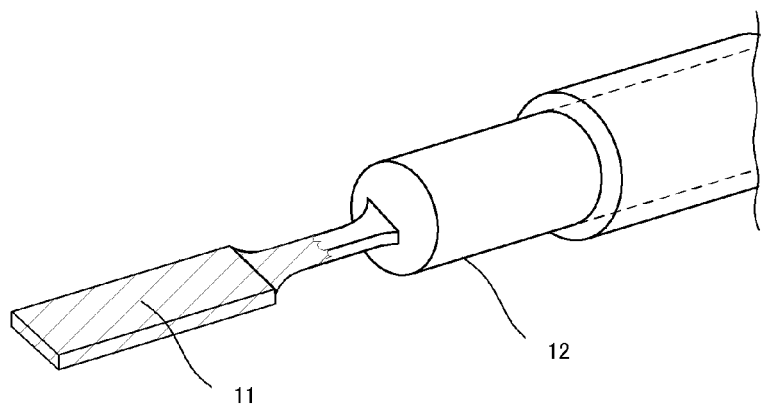
FIG. 7B provides a schematic drawing that illustrates a formation example of a first coating on a surgical electrode.
Figure 7C:
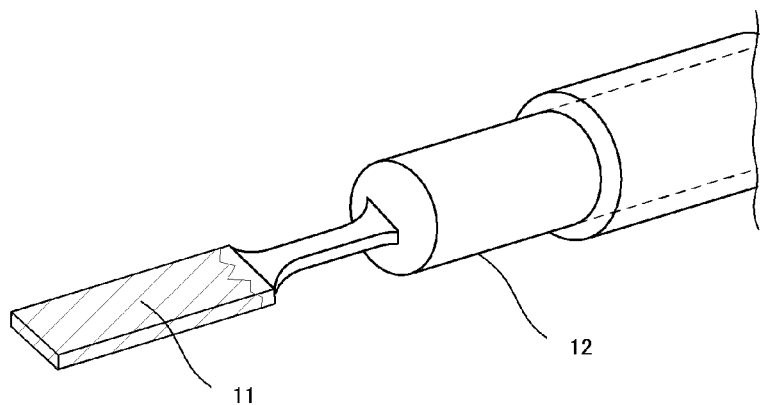
FIG. 7C provides a schematic drawing that illustrates formation examples of a first coating on a surgical electrode.

In one example, the first coating formed by the first and the second steps may be formed on the entire surface of the blade part of the end portion 11 as illustrated with hatching in FIG. 7A or on the blade part of the end portion 11 and a part of the intermediate connecting part as illustrated with hatching in FIG. 7B, or may be formed on a part away from the electrical connection portion 13 in the blade part of the end portion 11 as illustrated in FIG. 7C (the first coating is not formed on a part close to the intermediate connecting part).

Figure 8A:
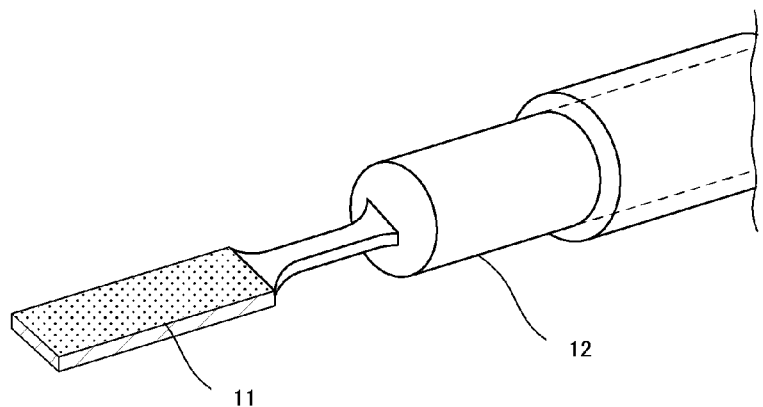
FIG. 8A provides a schematic drawing that illustrates formation examples of a first coating and a second film on a surgical electrode.
Figure 8B:
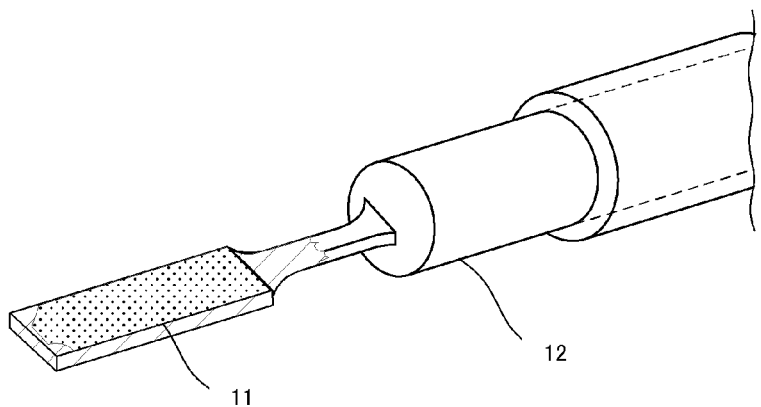
FIG. 8B provides a schematic drawing that illustrates formation examples of a first coating and a second film on a surgical electrode.

In another example, the second film formed by the third and the fourth steps may be formed on the entire surface of the flat part (both the upper surface and the lower surface of the blade part) in the end portion as illustrated with a dot pattern in FIG. 8A, and the second film is not formed on the side surfaces (surfaces other than the flat part) of the blade part. In yet another example, as illustrated with a dot pattern in FIG. 8B, the second film is formed on neither the side surfaces of the blade part nor the distal ends of the upper and the lower surfaces. In this manner, by not forming the second film on the side surfaces as well as the distal ends, particularly the corners of the upper and the lower surfaces (parts away from the electrical connection portion 13), a high frequency can be sufficiently emitted from the part of the end portion that can come into close contact with a living tissue and the like, namely a part that discharges electricity (hereinafter, referred to as "discharging part"); therefore, a surgical electrode instrument can be ensured to have good incision capability. In cases where the second film is formed on the side surfaces as well as the distal ends, particularly the corners of the upper and the lower surfaces, it is preferred to control the film thickness to be small (e.g., 10 μm or less, preferably 5 μm or less, more preferably 2 μm or less). By this, a high frequency can be sufficiently emitted from the discharging part that can come into close contact with a living tissue, so that deterioration of the incision capability can be inhibited.

In the end portion having the surface treatment film (a blade part in the case of a blade-type surgical electrode), the amount of the first coating is not particularly restricted; however, it is preferably in a range of 0.1 mg/m² to 50 mg/m², more preferably in a range of 1 mg/m² to 40 mg/m². When the first coating is formed from an amino group-containing silane coupling agent, it is preferred that the amount of the first coating be in the above-described range in terms of $SiO_2$-equivalent mass.

The amount of the first coating can be determined by measuring the coating amount on a metal material having a prescribed area. Further, when the first coating is formed from an amino group-containing silane coupling agent, the coating amount can be determined by analyzing the first coating by a fluorescent X-ray method, calculating the mass in terms of $SiO_2$ from the Si intensity, and then determining the coating amount per unit area.

Moreover, the total film thickness of the surface treatment film, which is formed on the end portion (a blade part in the case of a blade-type surgical electrode) and includes the first coating and the second film, is preferably in a range of 10 μm to 400 μm, more preferably in a range of 20 μm to 300 μm, still more preferably in a range of 30 μm to 200 μm, particularly preferably in a range of 50 μm to 150 μm.

Examples

The actions and effects of the present invention will now be described concretely by way of Examples. It is noted here, however, that the following descriptions of Examples do not restrict the scope of the present invention by any means.

(1) Preparation of Surgical Electrodes

Blade-type surgical electrodes having a plate-form end portion 11 as illustrated in FIG. 1 were prepared. The material and the blade part size of each of the thus prepared surgical electrodes are shown below. The surface roughness (arithmetic average roughness: Ra) of the blade part was measured using a three-dimensional surface roughness analyzer (model: SURFCOM 570A, manufactured by Tokyo Seimitsu Co., Ltd.). The measurement was performed by 2.0-mm scanning at a rate of 0.3 mm/s.

(Z1) Material of surgical electrode: stainless steel SUS304
Size of blade part: 0.3 mm in plate thickness, 17.0 mm in length, 2.5 mm in width (Z2) Material of surgical electrode: stainless steel SUS316L
Size of blade part: 0.3 mm in plate thickness, 17.0 mm in length, 2.5 mm in width The blade part of each surgical electrode was immersed in ethanol (special grade, manufactured by Junsei Chemical Co., Ltd.) and ultrasonicated for 10 minutes to remove oil and dirt from the surface. Subsequently, the blade part was dried at 100° C. for 10 minutes to remove ethanol adhering thereto.

(2) Preparation of Surface Treatment Agents

As surface treatment agents (X), solutions were prepared by mixing the respective S1 to S7 shown in Table 1 below with ethanol such that the resulting solutions had a solid mass concentration of 1.0%.

Surface treatment agents (Y) were prepared by mixing the components shown in Tables 2 to 5 at the respective ratios shown in Table 6. It is noted here that the thus prepared surface treatment agents (Y) had a viscosity of 7.0 Pa·s. The viscosity was measured at 25° C. using a vibration-type viscometer (VM Series, manufactured by Sekonic Corporation).

In Table 6, the values in the columns of "% by mass" under "Silicone resin (A)", "Compound (B)" and "Silane coupling agent (D)" each indicate the mass ratio of each component with respect to a total mass of these components. Further, in Table 6, the values in the column of "% by mass" under "Aromatic hydrocarbon-based solvent (C)" each indicate the mass ratio of the aromatic hydrocarbon-based solvent (C) with respect to a total mass of the corresponding surface treatment agent. In Table 6, "$B_M/A_M$" represents a ratio of the total mass ($B_M$) of the compound (B) to the total mass ($A_M$) of the silicone resin (A). Moreover, in Table 6, "$D_M/A_M$" represents a ratio of the total mass ($D_M$) of the silane coupling agent (D) to the total mass ($A_M$) of the silicone resin (A).

[Table 1]

TABLE 1

| # | Surface treatment |
|---|---|
| S1 | 3-aminopropyltriethoxy silane (manufactured by Shin-Etsu Chemical Co., Ltd., KBE-903) |
| S2 | N-2-(aminoethyl)-3-aminopropyltrimethoxy silane (manufactured by Shin-Etsu Chemical Co., Ltd., KBM-603) |
| S3 | 3-ureidopropyltrialchoxy silane (manufactured by Shin-Etsu Chemical Co., Ltd., KBE-585) |
| S4 | Silicone resin (manufactured by Shin-Etsu Chemical Co., Ltd., KR-5206) |
| S5 | Polyethyleneimine (manufactured by Nippon Shokubai Co., Ltd., Epomine P-1000) |
| S6 | Pethylated meramine resin (manufactured by Chang Chun Plastics Co., Ltd., Chang Chun meramine resin M-30WT) |
| S7 | Polyallylamine (manufactured by Nittobo Medical Co., Ltd., PAA-D19) |

[Table 2]

TABLE 2

| # | Silicone resine (A) |
|---|---|
| A1 | Epoxy resin-type silicone resin (manufactured by Shin-Etsu Chemical Co., Ltd., ES-1002T) |
| A2 | Mixture of a polydimethyl siloxiane copolymer capped with terminals of its molecular chain (weight-average molecular weight: 6000) and a methylhydrogen siloxane-dimethyl siloxane copolymer capped by trimethylsilyl groups at both terminals of its molecular chain (manufactured by Shin-Etsu Chemical Co., Ltd.) |
| A3 | Mixture of a polydimethyl siloxane copolymer capped with terminals of its molecular chain (weight-average molecular weight: 6500) and a methylhydrogen siloxane-dimethyl siloxane copolymer capped by trimethylsilyl groups at both terminals of its molecular chain (manufactured by Shin-Etsu Chemical Co., Ltd.) |
| A4 | Mixture of a polydimethyl siloxane copolymer capped with terminals of its molecular chain (weight-average molecular weight: 8000) and a methylhydrogen siloxane-dimethyl siloxane copolymer capped by trimethylsilyl groups at both terminals of its molecular chain (manufactured by Shin-Etsu Chemical Co., Ltd., KR-165) |
| A5 | Mixture of a polydimethyl siloxane copolymer capped with terminals of its molecular chain (weight-average molecular weight: 40000) and a methylhydrogen siloxane-dimethyl siloxane copolymer capped by trimethylsilyl groups at both terminals of its molecular chain (manufactured by Shin-Etsu Chemical Co., Ltd.) |
| A6 | Mixture of a polydimethyl siloxane copolymer capped with terminals of its molecular chain (weight-average molecular weight: 45000) and a methylhydrogen siloxane-dimethyl siloxane copolymer capped by trimethylsilyl groups at both terminals of its molecular chain (manufactured by Shin-Etsu Chemical Co., Ltd.) |

[Table 3]

TABLE 3

| # | Compound (B) |
|---|---|
| B1 | $H_2PtCl_4 \cdot nH_2O$ (manufactured by Shin-Etsu Chemical Co., Ltd., D-168) |
| B2 | $Ti(C_3H_3O)_2(C_5H_7O_2)_2$ (manufactured by Matsumoto Fine Chemical Co., Ltd., TC-100) |

[Table 4]

TABLE 4

| # | Aromatic hydrocarbon-based solvent (C) |
|---|---|
| C1 | Xylene (SP value: 8.9) |
| C2 | Benzene (SP value: 9.2) |

[Table 5]

TABLE 5

| # | Silane coupling agent (D) |
|---|---|
| D1 | Vinyltrimethoxy silane (Shin-Etsu Chemical Co., Ltd., KBM-1003) |
| D2 | 3-glycydoxypropyltrimethoxy silane (Shin-Etsu Chemical Co., Ltd., KBM-403) |

[Table 6]

TABLE 6

| | Silicone resin (A) | | Compound (B) | | Aromatic hydrocarbon-based solvent (C) | | Silane coupling agent (D) | | % by mass $B_M/A_M$ | % by mass $D_M/A_M$ |
|---|---|---|---|---|---|---|---|---|---|---|
| | Type | % by mass | Type | % by mass | Type | % by mass | Type | % by mass | | |
| Y1 | A1 | 99.6% | B1 | 0.4% | C1 | 70.0% | — | — | 0.004 | — |
| Y2 | A2 | 99.6% | B1 | 0.4% | C1 | 70.0% | — | — | 0.004 | — |
| Y3 | A3 | 99.6% | B1 | 0.4% | C1 | 70.0% | — | — | 0.004 | — |
| Y4 | A4 | 99.6% | B1 | 0.4% | C1 | 70.0% | — | — | 0.004 | — |
| Y5 | A5 | 99.6% | B1 | 0.4% | C1 | 70.0% | — | — | 0.004 | — |
| Y6 | A6 | 99.6% | B1 | 0.4% | C1 | 70.0% | — | — | 0.004 | — |
| Y7 | A4 | 90.0% | B1 | 10.0% | C1 | 70.0% | — | — | 0.111 | — |

TABLE 6-continued

|   | Silicone resin (A) | | Compound (B) | | Aromatic hydrocarbon-based solvent (C) | | Silane coupling agent (D) | | % by mass $B_M/A_M$ | % by mass $D_M/A_M$ |
| --- | --- | --- | --- | --- | --- | --- | --- | --- | --- | --- |
|   | Type | % by mass | Type | % by mass | Type | % by mass | Type | % by mass | | |
| Y8  | A4 | 95.0% | B1 | 5.0% | C1 | 70.0% | — | — | 0.053 | — |
| Y9  | A4 | 98.0% | B1 | 2.0% | C1 | 70.0% | — | — | 0.020 | — |
| Y11 | A4 | 99.7% | B1 | 0.3% | C1 | 70.0% | — | — | 0.003 | — |
| Y12 | A4 | 99.8% | B1 | 0.2% | C1 | 70.0% | — | — | 0.002 | — |
| Y13 | A4 | 99.9% | B1 | 0.1% | C1 | 70.0% | — | — | 0.001 | — |
| Y14 | A4 | 99.6% | B2 | 0.4% | C1 | 70.0% | — | — | 0.004 | — |
| Y15 | A4 | 99.6% | B1 | 0.4% | C2 | 70.0% | — | — | 0.004 | — |
| Y16 | A4 | 99.1% | B1 | 0.4% | C1 | 70.0% | D1 | 0.5% | 0.004 | 0.005 |
| Y17 | A4 | 98.6% | B1 | 0.4% | C1 | 70.0% | D1 | 1.0% | 0.004 | 0.010 |
| Y18 | A4 | 96.6% | B1 | 0.4% | C1 | 70.0% | D1 | 3.0% | 0.004 | 0.031 |
| Y19 | A4 | 89.6% | B1 | 0.4% | C1 | 70.0% | D1 | 10.0% | 0.004 | 0.112 |
| Y20 | A4 | 79.6% | B1 | 0.4% | C1 | 70.0% | D1 | 20.0% | 0.005 | 0.251 |
| Y21 | A4 | 96.6% | B1 | 0.4% | C1 | 70.0% | D2 | 3.0% | 0.004 | 0.031 |

(3) Production of End Portion 11 Having Surface Treatment Film

The blade part removed of oil and dirt was immersed in each surface treatment agent (X). After the immersion, the blade part was dried at 100° C. for 10 minutes to obtain a surgical electrode having a first coating. In those cases where the first coating was formed using any one of S1 to S4, the first coating was analyzed by a fluorescent X-ray method, and the mass was calculated in terms of $SiO_2$ from the Si intensity to determine the coating amount per unit area. Meanwhile, in those cases where the first coating was formed using any one of S5 to S7, the coating amount on the blade part having a prescribed area on which the first coating was formed in the above-described manner was measured to determine the coating amount per unit area.

Next, on the flat parts (both surfaces) of the end portion 11 having the thus formed first coating, each surface treatment agent (Y) shown in Table 7 was applied using the below-described dispenser and subsequently dried for 30 minutes at the drying temperature shown in Table 7, whereby surgical electrodes of Examples 1 to 47 and Comparative Examples 1 to 4, each of which had a second film of a prescribed thickness (see Table 7), were obtained.

Dispenser (desktop-type robot): manufactured by Musashi Engineering, Inc., trade name: ML-808GX, SM4000 MEGAX-3A-SS (4) Evaluation Tests The thus obtained surgical electrodes of Examples 1 to 47 and Comparative Examples 1 to 4 were each electrically connected to the below-described electrosurgical instrument main body. Further, a counter electrode plate electrically connected to the electrosurgical instrument main body was attached to a stainless-steel container in which a porcine liver was placed.

<Electrosurgical Instrument Main Body (High-Frequency Apparatus and Control Pencil)>

High-frequency apparatus: EXCALIBUR Plus PC, medical device approval No.: 20700BZY01171

Control pencil: manufactured by Japan Medicalnext Co., Ltd., disposable control pencil, medical device approval No.: 20300BZY01003000

(4-1) Evaluation by Pure Cutting Mode (30 W)

The electrosurgical instrument main body was operated in the pure cutting mode (output: 30 W), and the blade part was inserted in the vertical direction at an angle of 45° with respect to the porcine liver surface. At a depth of 12 mm, the thus inserted blade part was moved by 60 mm parallel to the porcine liver surface at a speed of 20 mm/s. This cutting operation was repeated twice, and the adhesion and the burn resistance were evaluated for the part of the blade part that was inserted into the porcine liver as the evaluation part.

Adhesion

Each surgical electrode used for the two repeated cutting operations was cooled to room temperature, and the evaluation part was subsequently held with fingers through a piece of gauze and wiped once. Thereafter, the film of the evaluation part was visually observed, and the adhesion was evaluated based on the following evaluation criteria. The results thereof are shown in Table 7.

S: The area of peeled film was less than 1% with respect to the evaluation part.

A: The area of peeled film was 1% to less than 5% with respect to the evaluation part.

B: The area of peeled film was 5% to less than 15% with respect to the evaluation part.

C: The area of peeled film was 15% or more with respect to the evaluation part.

Burn Resistance

Each surgical electrode used for the two repeated cutting operations was cooled to room temperature, and the evaluation part was subsequently held with fingers through a piece of gauze and wiped once. Thereafter, the ratio of the area that was burned and turned black in the evaluation part was quantified, and the burn resistance was evaluated based on the following evaluation criteria. The results thereof are shown in Table 7.

A: The ratio of such area was 0% to lower than 5%.

B: The ratio of such area was 5% to lower than 20%.

C: The ratio of such area was 20% or higher.

(4-2) Evaluation by Pure Cutting Mode (80 W)

The adhesion and the burn resistance were evaluated in the same manner as in the above (4-1), except that the output in the pure cutting mode of the electrosurgical instrument main body was changed to 80 W. The results thereof are shown in Table 7.

[Table 7]

TABLE 7

| Example/ Comperative Example | Surgical electrode | Surface roughness of the blade part Ra | First coating | | Second film | | | | Pure cutting mode | | | | | |
|---|---|---|---|---|---|---|---|---|---|---|---|---|---|---|
| | | | Amino group-containing compound | Coating amount mg/m² | Drying temperature °C. | Surface treatment agent (Y) | Film thickness μm | Drying temperature °C. | 30 W | | | 80 W | | |
| | | | | | | | | | Adhesion | Burned area (%) | Burn resistance | Adhesion | Burned area (%) | Burn resistance |
| Example1 | Z1 | 0.14 | S1 | 10 | 100 | Y4 | 100 | 150 | S | 2 | A | A | 3 | A |
| Example2 | Z1 | 0.14 | S2 | 10 | 100 | Y4 | 100 | 150 | S | 2 | A | A | 3 | A |
| Example3 | Z1 | 0.14 | S3 | 10 | 100 | Y4 | 100 | 150 | A | 2 | A | A | 3 | A |
| Example4 | Z1 | 0.14 | S1 | 0.1 | 100 | Y4 | 100 | 150 | A | 2 | A | A | 3 | A |
| Example5 | Z1 | 0.14 | S1 | 1 | 100 | Y4 | 100 | 150 | S | 2 | A | A | 3 | A |
| Example6 | Z1 | 0.14 | S1 | 40 | 100 | Y4 | 100 | 150 | S | 2 | A | A | 3 | A |
| Example7 | Z1 | 0.14 | S1 | 50 | 100 | Y4 | 100 | 150 | A | 2 | A | A | 3 | A |
| Example8 | Z1 | 0.14 | S1 | 10 | 40 | Y4 | 100 | 150 | A | 2 | A | A | 3 | A |
| Example9 | Z1 | 0.14 | S1 | 10 | 60 | Y4 | 100 | 150 | A | 2 | A | A | 3 | A |
| Example10 | Z1 | 0.14 | S1 | 10 | 80 | Y4 | 100 | 150 | S | 2 | A | A | 3 | A |
| Example11 | Z1 | 0.14 | S1 | 10 | 180 | Y4 | 100 | 150 | S | 2 | A | A | 3 | A |
| Example12 | Z1 | 0.14 | S1 | 10 | 250 | Y4 | 100 | 150 | S | 2 | A | A | 3 | A |
| Example13 | Z1 | 0.14 | S1 | 10 | 100 | Y1 | 100 | 150 | S | 4 | A | A | 4 | A |
| Example14 | Z1 | 0.14 | S1 | 10 | 100 | Y2 | 100 | 150 | S | 3 | A | A | 4 | A |
| Example15 | Z1 | 0.14 | S1 | 10 | 100 | Y3 | 100 | 150 | S | 2 | A | A | 3 | A |
| Example16 | Z1 | 0.14 | S1 | 10 | 100 | Y5 | 100 | 150 | S | 2 | A | A | 3 | A |
| Example17 | Z1 | 0.14 | S1 | 10 | 100 | Y6 | 100 | 150 | S | 3 | A | A | 4 | A |
| Example18 | Z1 | 0.14 | S1 | 10 | 100 | Y7 | 100 | 150 | A | 3 | A | A | 3 | A |
| Example19 | Z1 | 0.14 | S1 | 10 | 100 | Y8 | 100 | 150 | S | 2 | A | A | 3 | A |
| Example20 | Z1 | 0.14 | S1 | 10 | 100 | Y9 | 100 | 150 | S | 2 | A | A | 3 | A |
| Example21 | Z1 | 0.14 | S1 | 10 | 100 | Y11 | 100 | 150 | S | 2 | A | A | 3 | A |
| Example22 | Z1 | 0.14 | S1 | 10 | 100 | Y12 | 100 | 150 | S | 2 | A | A | 3 | A |
| Example23 | Z1 | 0.14 | S1 | 10 | 100 | Y13 | 100 | 150 | S | 3 | A | A | 3 | A |
| Example24 | Z1 | 0.14 | S1 | 10 | 100 | Y14 | 100 | 150 | S | 2 | A | A | 3 | A |
| Example25 | Z1 | 0.14 | S1 | 10 | 100 | Y15 | 100 | 150 | S | 2 | A | A | 3 | A |
| Example26 | Z1 | 0.14 | S1 | 10 | 100 | Y16 | 100 | 150 | S | 2 | A | A | 3 | A |
| Example27 | Z1 | 0.14 | S1 | 10 | 100 | Y17 | 100 | 150 | S | 2 | A | A | 3 | A |
| Example28 | Z1 | 0.14 | S1 | 10 | 100 | Y18 | 100 | 150 | S | 2 | A | S | 3 | A |
| Example29 | Z1 | 0.14 | S1 | 10 | 100 | Y19 | 100 | 150 | S | 3 | A | A | 4 | A |
| Example30 | Z1 | 0.14 | S1 | 10 | 100 | Y20 | 100 | 150 | S | 3 | A | A | 4 | A |
| Example31 | Z1 | 0.14 | S1 | 10 | 100 | Y21 | 100 | 150 | S | 2 | A | S | 3 | A |
| Example32 | Z1 | 0.14 | S1 | 10 | 100 | Y4 | 10 | 150 | S | 4 | A | A | 4 | A |
| Example33 | Z1 | 0.14 | S1 | 10 | 100 | Y4 | 20 | 150 | S | 3 | A | A | 4 | A |
| Example34 | Z1 | 0.14 | S1 | 10 | 100 | Y4 | 300 | 150 | A | 2 | A | A | 3 | A |
| Example35 | Z1 | 0.14 | S1 | 10 | 100 | Y4 | 400 | 150 | A | 2 | A | A | 3 | A |
| Example36 | Z1 | 0.14 | S1 | 10 | 100 | Y4 | 100 | 40 | A | 3 | A | A | 4 | A |
| Example37 | Z1 | 0.14 | S1 | 10 | 100 | Y4 | 100 | 60 | A | 3 | A | A | 4 | A |
| Example38 | Z1 | 0.14 | S1 | 10 | 100 | Y4 | 100 | 180 | S | 2 | A | A | 3 | A |
| Example39 | Z1 | 0.14 | S1 | 10 | 100 | Y4 | 100 | 250 | S | 3 | A | A | 4 | A |
| Example40 | Z2 | 0.14 | S1 | 10 | 100 | Y4 | 100 | 150 | S | 2 | A | A | 3 | A |
| Example41 | Z1 | 0.14 | S5 | 40 | 100 | Y4 | 100 | 150 | A | 2 | A | A | 4 | A |
| Example42 | Z1 | 0.14 | S6 | 40 | 100 | Y4 | 100 | 150 | A | 2 | A | A | 3 | A |
| Example43 | Z1 | 0.14 | S7 | 40 | 100 | Y4 | 100 | 150 | A | 2 | A | A | 3 | A |
| Example44 | Z1 | 0.05 | S1 | 10 | 100 | Y4 | 100 | 150 | S | 2 | A | A | 3 | A |
| Example45 | Z1 | 0.39 | S1 | 10 | 100 | Y4 | 100 | 150 | S | 2 | A | A | 3 | A |
| Example46 | Z1 | 0.01 | S1 | 10 | 100 | Y4 | 100 | 150 | A | 2 | A | A | 3 | A |
| Example47 | Z1 | 0.45 | S1 | 10 | 100 | Y4 | 100 | 150 | A | 2 | A | A | 3 | A |
| C. Example1 | Z1 | 0.14 | — | 0.0 | 100 | Y4 | 100 | 150 | B | 10 | B | C | 18 | B |
| C. Example2 | Z1 | 0.14 | S4 | 10 | 100 | Y4 | 100 | 150 | C | 45 | C | C | 65 | C |
| C. Example3 | Z1 | 0.14 | — | — | — | — | — | — | C | 90 | C | C | 95 | C |
| C. Example4 | Z1 | 0.14 | S1 | 10 | 100 | — | — | — | C | 90 | C | C | 95 | C |

The present invention has been described above in detail referring to concrete examples thereof; however, it is obvious to those skilled in the art that various modifications and changes can be made without departing from the gist and the scope of the present invention.

DESCRIPTION OF SYMBOLS

10, 20, 30, 40, 60: surgical electrode
11, 21, 31, 41, 61: end portion
12: intermediate portion
13, 23, 33, 43: electrical connection portion
14, 24, 34, 44: cover

The invention claimed is:

1. A surgical electrode of an electrosurgical instrument used for surgery of a living tissue, wherein
the surgical electrode comprises an end portion capable of emitting a high frequency,
the end portion has a surface treatment film which comprises a first coating and a second film in the order mentioned,
the first coating is formed by contacting a surface treatment agent (X) with or over the entirety or a part of the surface of the end portion at least, which surface treatment agent (X) comprises at least an amino group-containing compound that is at least one selected from the group consisting of a homopolymer of a melamine resin, a copolymer containing a melamine resin, an amino group-containing silane coupling agent, and polyallylamine, a total content of the amino group-containing compound in the surface treatment agent (X) is in a range of 0.1% by mass to 10% by mass, an amount of the first coating is in a range of 1 mg/m$^2$ to 40 mg/m$^2$, and the second film is formed by contacting a surface treatment agent (Y) with the entirety or a part of the surface of the first coating, which surface treatment agent (Y) comprises: a silicone resin (A); a compound (B) containing a metal element selected from titanium, platinum, rhodium and palladium; and an aromatic hydrocarbon-based solvent (C), and satisfies:

(I) the content of the silicone resin (A) is in a range of 90% by mass to 99.9% by mass with respect to a total solid mass of the silicone resin (A) and the compound (B); and (II) a ratio ($B_M/A_M$) of a mass ($B_M$) of the compound (B) to a mass ($A_M$) of the silicone resin (A) is in a range of 0.001 to 0.111.

2. The surgical electrode according to claim 1, wherein the surface treatment agent (Y) further comprises a vinyl group-containing silane coupling agent and/or an epoxy group-containing silane coupling agent, and a ratio ($D_M/A_M$) of a total mass ($D_M$) of the vinyl group-containing silane coupling agent and/or the epoxy group-containing silane coupling agent to the mass ($A_M$) is in a range of 0.005 to 0.251.

3. The surgical electrode according to claim 1, wherein a weight-average molecular weight of the silicone resin (A) is in a range of 6,000 to 45,000.

\* \* \* \* \*